United States Patent
Kanemaru et al.

(10) Patent No.: US 12,325,218 B2
(45) Date of Patent: Jun. 10, 2025

(54) JIG

(71) Applicant: Panasonic Intellectual Property Management Co., Ltd., Osaka (JP)

(72) Inventors: Hiroshi Kanemaru, Osaka (JP); Mari Ueda, Osaka (JP); Sachiko Takeshita, Tokyo (JP)

(73) Assignee: PANASONIC INTELLECTUAL PROPERTY MANAGEMENT CO., LTD., Osaka (JP)

( * ) Notice: Subject to any disclaimer, the term of this patent is extended or adjusted under 35 U.S.C. 154(b) by 151 days.

(21) Appl. No.: 17/913,345

(22) PCT Filed: Oct. 1, 2020

(86) PCT No.: PCT/JP2020/037454
§ 371 (c)(1),
(2) Date: Sep. 21, 2022

(87) PCT Pub. No.: WO2021/192369
PCT Pub. Date: Sep. 30, 2021

(65) Prior Publication Data
US 2023/0115616 A1    Apr. 13, 2023

(30) Foreign Application Priority Data

Mar. 26, 2020  (JP) .................................. 2020-055790
Mar. 27, 2020  (JP) .................................. 2020-058596

(51) Int. Cl.
| | |
|---|---|
| *B32B 37/00* | (2006.01) |
| *B32B 5/18* | (2006.01) |
| *A45D 44/00* | (2006.01) |

(52) U.S. Cl.
CPC ............ *B32B 37/0046* (2013.01); *B32B 5/18* (2013.01); *B32B 37/025* (2013.01); *A45D 44/00* (2013.01);
(Continued)

(58) Field of Classification Search
CPC ..... B32B 37/0046; B32B 5/18; B32B 37/025; B32B 2305/022; B32B 2307/536;
(Continued)

(56) References Cited

U.S. PATENT DOCUMENTS

| | | |
|---|---|---|
| 2019/0098149 A1 | 3/2019 | Shinoda |
| 2019/0200726 A1 | 7/2019 | Shinoda et al. |
| 2020/0170381 A1* | 6/2020 | Park ..................... A45D 44/002 |

FOREIGN PATENT DOCUMENTS

| | | |
|---|---|---|
| JP | 2013-119676 | 6/2013 |
| JP | 2013119676 A * | 6/2013 |

(Continued)

OTHER PUBLICATIONS

English Translation of Shindo JP2013119676, generated Apr. 19, 2024, Espacenet (Year: 2013).*

(Continued)

*Primary Examiner* — Andrew L Swanson
(74) *Attorney, Agent, or Firm* — GREENBLUM & BERNSTEIN, P.L.C.

(57) ABSTRACT

Provided is a jig which assists in the adhesion of a thin-film sheet to an adhesion target surface (skin etc.), and which can easily adhere the thin-film sheet to the adhesion target surface. The jig includes: a base part having a first surface; and a porous hydrophilic film that is adhered to the first surface and has fine pores with a predetermined porosity, wherein the porosity is 35% to 55% inclusive. The hardness of the base part is preferably 4-20 inclusive. In addition, it is preferable that the base part and the hydrophilic film have transparency.

11 Claims, 6 Drawing Sheets

(52) U.S. Cl.
CPC ... *B32B 2305/022* (2013.01); *B32B 2307/536* (2013.01); *B32B 2307/728* (2013.01)

(58) Field of Classification Search
CPC .............. B32B 2307/728; A45D 44/00; A45D 2200/1027; A45D 40/00; A45D 44/002; A45D 44/22; A45D 2200/1036; A45D 33/38; A45D 40/30; A61Q 1/02; A61K 2800/87
See application file for complete search history.

(56) References Cited

FOREIGN PATENT DOCUMENTS

| | | | | |
|---|---|---|---|---|
| JP | 2015-43836 | 3/2015 | | |
| WO | 2018/003421 | 1/2018 | | |
| WO | 2018/061486 | 4/2018 | | |
| WO | WO-2018061486 A1 * | 4/2018 | ............. | A45D 34/04 |

OTHER PUBLICATIONS

English Translation of Shinoda WO2018061486A1, US Patent Application Publication U.S. Patent Application Publication 20190200726 (Year: 2018).*

International Search Report issued in International Patent Application No. PCT/JP2020/037454, dated Nov. 10, 2020.

* cited by examiner

JIG

TECHNICAL FIELD

The present disclosure relates to a jig that assists in attaching a thin sheet to a target surface (e.g., skin).

BACKGROUND ART

A technique known in the related art proposes that a dark spot, blotch, or scar (hereinafter, also referred to as a "discolored region"), or the like on the skin are made less noticeable by attaching a thin film coated with ink containing various colorants to the human body (e.g., PTL 1). In the technique disclosed in PTL 1, the discolored region is identified by imaging the skin. A color similar to the color around the discolored region is printed on a thin sheet, and the thin sheet is attached to the skin to make the discolored region less noticeable.

Such a thin sheet is usually distributed in the form of a multilayer sheet including a thin sheet on a base sheet. The thin sheet is separated from the base sheet and attached to the skin by a user. It is, however, difficult to attach the thin sheet to the skin without generating wrinkles and the like because the thin sheet is very thin. To deal with this, a method for attaching the thin sheet to the skin by using a jig is proposed in PTL 2. For example, a multilayer sheet is disposed on a jig such that the thin sheet faces the jig, and water is sprayed to the base sheet. The base sheet is separated off, and the exposed thin sheet is brought into close contact with the skin. The jig is then separated from the thin sheet.

CITATION LIST

Patent Literature

PTL 1
Japanese Patent Application Laid-Open No. 2015-43836
PTL 2
WO 2018/061486

SUMMARY OF INVENTION

Technical Problem

However, the thin sheet may be difficult to separate from the jig when the thin sheet is transferred from the jig to a target surface because the thin sheet is very thin. In addition, when the thin sheet is attached to the target surface by using the jig, pressure is not evenly applied to the thin sheet because of irregularities on the target surface, and part of the thin sheet may not come into close contact with the target surface.

The present disclosure is directed to a jig that facilitates attachment of a thin sheet to a target surface.

Solution to Problem

The present disclosure provides the following jig:
a jig that assists in attaching a thin sheet to a target surface, the jig comprising:
a substrate having a first surface;
a porous hydrophilic film attached to the first surface and having fine pores with a predetermined porosity, wherein the porosity is 35% or more and 55% or less.

Advantageous Effects of Invention

A jig according to the present disclosure facilitates attachment of a thin sheet to a target surface.

DESCRIPTION OF EMBODIMENTS

Embodiments

Figure 1:
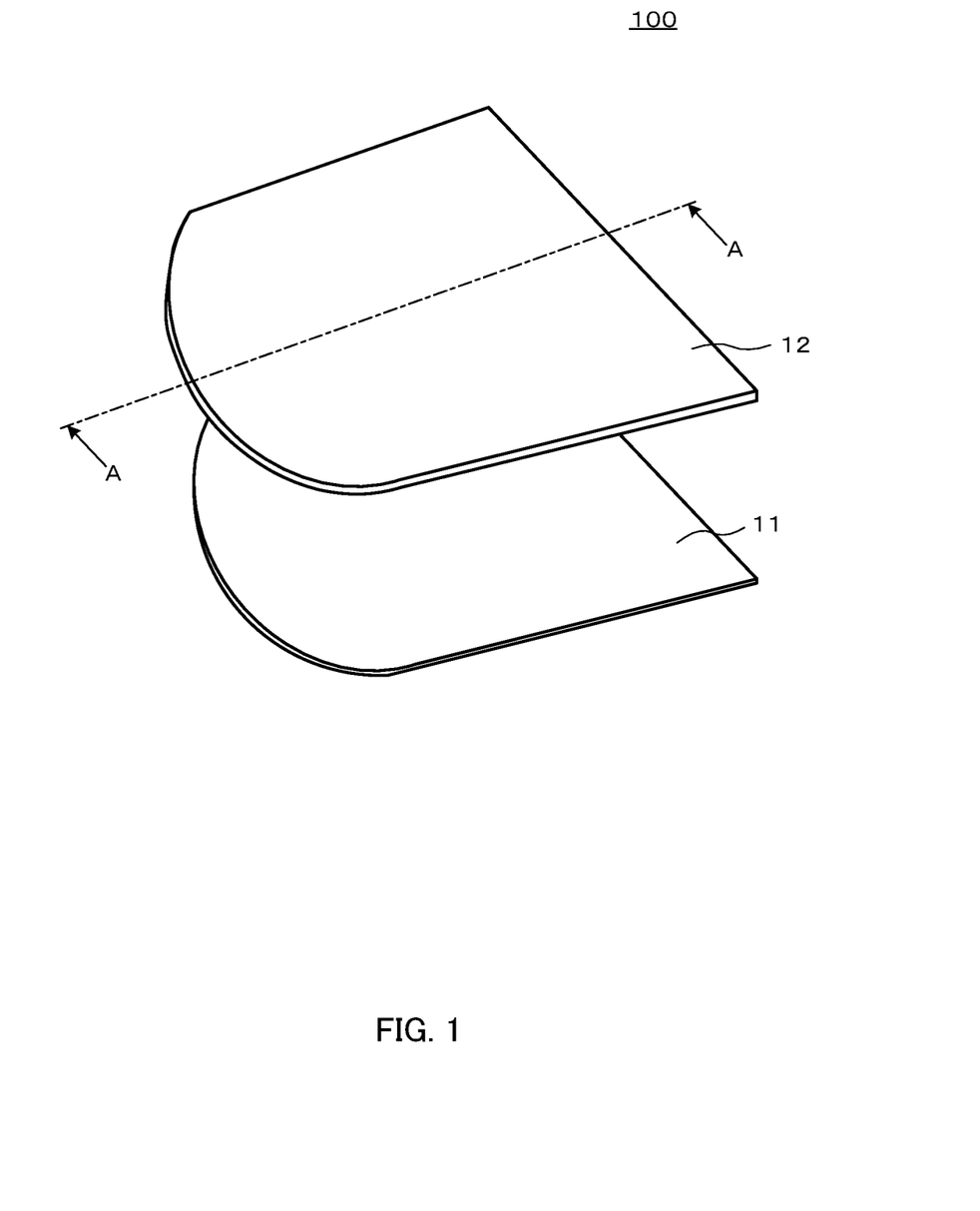
FIG. 1 is an exploded perspective view of a multilayer sheet according to Embodiment 1 of the present disclosure.

Embodiment 1 of the present disclosure will be described below in detail with reference to the drawings.
[Multilayer Sheet]
First, the structure of multilayer sheet 100 according to Embodiment 1 is described with reference to FIG. 1. Multilayer sheet 100 of Embodiment 1 has a multilayer structure including support 12 and thin sheet 11 to be attached to the skin. The multilayer sheet may be a rolled sheet or a single sheet. In the case where the multilayer sheet is a rolled sheet, the sheet is unrolled to the required length before use. In the case where the multilayer sheet is a rolled sheet, a cut line (cut) or the like may be formed to cut the multilayer sheet at a desired length.
(Thin Sheet)
Thin sheet 11 may be a sheet (sheet produced on demand) intended for use by a specific person and produced according to a discolored area of the skin of the specific person through a known make-up support system or the like. Thin sheet 11 may be, for example, a sheet intended for use by an unspecified number of people and produced according to the average skin color of an unspecified number of people. Thin sheet 11 can be used not only for coloring the skin or the like but also for making the discolored area less noticeable or decorating the discolored area when being attached to the discolored area of the skin.

Thin sheet 11 has a thickness of 10 µm or less for attachment to the skin. The thickness of thin sheet 11 is preferably 10 nm to 10 more preferably 10 nm to 1000 nm. The attachment of thin sheet 11 having a thickness in this range to a target surface, such as the skin, does not generate discomfort.

Thin sheet 11 can include, for example, a liquid-permeable thin film (not shown) and a coloring layer or a light-scattering layer or the like (not shown). In the case where thin sheet 11 has a coloring layer or a light-scattering layer or the like in addition to the thin film, the target surface (e.g., skin) can be colored with any color by attachment of thin sheet 11. More specifically, the skin can be colored, or the discolored area of the skin can be made appear normal in color. In the case where thin sheet 11 has a coloring layer or the like, thin sheet 11 is preferably attached to the target surface such that the thin film in thin sheet 11 is in contact with the target surface. In the case where the target surface is the human skin, thin sheet 11 is attached to the skin such that a biocompatible thin film is in contact with the skin to prevent or reduce irritation of the skin or the like. In the case where thin sheet 11 has a coloring layer, thin sheet 11 is placed on support 12 such that the thin film faces support 12 described below.

The thin film in thin sheet 11 is preferably a biocompatible sheet-shaped member that does not generate discomfort when being attached to the human skin. The thin film is usually preferably colorless and transparent, or translucent.

The thickness of the thin film in thin sheet 11 is preferably 10 nm to 10 µm, more preferably 10 nm to 1000 nm. In particular, in the case where the thin film is hydrophobic, the thinness of the film is particularly preferably 10 nm to 800 nm.

The shape of the thin film in plan view is not limited and appropriately selected according to the shape of the attachment site for thin sheet 11 and the intended use. The thin film may have a cut in an outer peripheral portion and/or in plane so as to conform to the shape of the attachment site for thin sheet 11.

The thin film may be a sheet formed by, for example, a spin coating method, a roll-to-roll method, or an LB method (Langmuir-Blodgett method), or a fiber sheet composed of folded fibers produced by electrospinning or the like.

Examples of the material of the thin film include polyesters, such as polyglycolic acid, polylactic acid, polycaprolactone, polyethylene succinate, polyethylene terephthalate, and copolymers thereof; polyethers, such as polyethylene glycol and polypropylene glycol; polyamides, such as Nylons, polyglutamic acid, polyaspartic acid, and salts thereof; polysaccharides, such as pullulan, cellulose, starch, chitin, chitosan, alginic acid, hyaluronic acid, cornstarch, and salts thereof; silicones, such as acrylic silicone and trimethylsiloxysilicic acid; acrylic acids, such as alkyl acrylates, silicone acrylate, acrylamide, and copolymers thereof; polyvinyl alcohol; polyurethanes; polycarbonates; polyacid anhydrides; polyethylene; polypropylene; porous layer coating sheets, and nanofiber sheets. In the case where the material of the thin film is polylactic acid, cellulose (e.g., carboxymethylcellulose or hydroxyethylcellulose), starch, chitin, chitosan, alginic acid, cornstarch, or polyurethane, the thin film has, for example, better biocompatibility, availability, and handleability.

The coloring layer placed on the thin film contains a colorant and a binder. The coloring layer may further contain, for example, a film-forming agent, a dispersant, and various additives. The color of the coloring layer is normally a color that works for the skin tone, but may be any color in the case where thin sheet 11 is used as cosmetics, such as blush, eyeshadow, and body painting. Thin sheet 11 may entirely have the same color but may partially have a different color region.

The coloring layer may be composed of one layer or may be composed of two or more layers. In the case where the coloring layer is composed of two or more layers, the layers may contain the same colorant or may contain different colorants. The amount of the colorant in the layers may be the same or different. For example, a coloring layer with a given color may be placed on a skin-coloring layer.

Examples of the colorant contained in the coloring layer include inorganic red pigments, such as iron oxide, iron hydroxide, and iron titanate; inorganic brown pigments, such as γ-iron oxide; inorganic yellow pigments, such as yellow iron oxide and ocher; inorganic black pigments, such as black iron oxide and carbon black; inorganic violet pigments, such as manganese violet and cobalt violet; inorganic green pigments, such as chromium hydroxide, chromium oxide, cobalt oxide, and cobalt titanate; inorganic blue pigments, such as Prussian blue (ferric ferrocyanide), ultramarine (ultramarine blue), lapis lazuli blue, mountain blue, aluminum-cobalt oxide, aluminum-zinc-cobalt oxide, silicon-cobalt oxide, silicon-zinc-cobalt oxide, cobalt pigments, smalt, cobalt blue, cobalt stannate, cobalt chromium blue, cobalt-aluminum-silicon oxide, and manganese blue; organic blue pigments and blue dyes, such as indigo, phthalocyanine, indanthrene blue, and sulfonates thereof; lakes produced from various tar-based dyes; lakes produced from various natural dyes; and composite synthetic resin powders produced by combining these powders.

The binder contained in the coloring layer may have any shape and preferably has a particle shape. In particular, the binder is preferably composed of particles made of (meth) acrylic resin (hereinafter referred to simply as "acrylic particles"). In the case where the binder is composed of acrylic particles, the colorant described above tends to have high fixability, and the coloring layer tends to have high durability. The binder is more preferably composed of particles of a (meth)acrylic resin that does not irritate the skin. The acrylic particles are thus preferably selected from, for example, components in the list of cosmetic ingredient labeling names based on the Pharmaceutical Affairs Law in Japan, components in accordance with EU cosmetics regulation (Cosmetics Directive 76/768/EEC), and components described in International Cosmetic Ingredient Dictionary and Handbook (Jan. 1, 2002, 9th edition) by the Cosmetic, Toiletry & Fragrance Association, U.S. (CTFA in the United States). The acrylic particles are preferably acrylic resin particles used in known cosmetics and the like.

The amount of the binder contained in the coloring layer is preferably 0.5 to 10 parts by mass, more preferably 1.5 to 5.7 parts by mass with respect to 10 parts by mass of the colorant. The presence of the binder in the above range with respect to the amount of the colorant improves fixability of the colorant. The presence of the binder in the above range also tends to provide a relatively sufficient amount of the colorant and thus allows the coloring layer to have a desired color.

The thickness of the coloring layer is appropriately selected according to the desired color depth or the like and preferably 10 nm to 15 µm, more preferably 10 nm to 3 µm. The coloring layer having a thickness in the above range tends to provide desired color formation without causing thick make-up. In the case where two or more coloring layers are layered, the total thickness of the layers is preferably in the above range. Such coloring layers can be formed by applying an ink containing a colorant and a binder on a thin film by, for example, ink-jet printing, screen printing, offset printing, or gravure printing. The ink may be oil-based ink or water-based ink. Of these methods, ink-jet printing is preferred in view of, for example, ease in on-demand printing, or multilayer printing in which cosmetic ink is applied multiple times.

The light-scattering layer contains a reflective material and a binder. The light-scattering layer may further contain, for example, a film-forming agent, a dispersant, and various additives. The light-scattering layer may be composed of one layer or may be composed of two or more layers. In the case where the light-scattering layer is composed of two or more layers, the layers may contain the same reflective material or may contain different reflective materials. The amount of the reflective material in the layers may be the same or different.

The reflective material contained in the light-scattering layer may be composed of particles that scatter or reflect ultraviolet light and visible light (e.g., light with wavelength of 200 nm to 780 nm) and may be, for example, a pearl agent, a soft focus agent, or a lame agent. Preferably, the pearl agent, the soft focus agent, and the lame agent do not irritate the skin.

The amount of the binder contained in the light-scattering layer is preferably 0.5 to 10 parts by mass, more preferably 1.5 to 5.7 parts by mass with respect to 10 parts by mass of the reflective material. The presence of the binder in the above range with respect to the amount of the reflective material improves fixability of the reflective material. The presence of the binder is in the above range also tends to provide a relatively sufficient amount of the reflective material and thus allows the light-scattering layer to sufficiently reflect or scatter light.

The thickness of the light-scattering layer is preferably 10 nm to 120 μm, more preferably 10 nm to 100 μm. The light-scattering layer having a thickness in this range tends to sufficiently reflect light reflected on the surface of the skin.

Thin sheet 11 may further include a glossy layer, a moisture-absorbing layer, and other layers unless the purpose and advantageous effects of Embodiment 1 are impaired. The moisture-absorbing layer controls the humidity on the surface of thin sheet 11 to improve comfort. The moisture-absorbing layer normally contains a moisture absorbent. Examples of the moisture absorbent include spherical silica, porous acrylic particles, and Nylon 6 (Polyamide 6).

(Support)

Support 12 is a plate-shaped member disposed on another surface of thin sheet 11 and functions as a base sheet that protects thin sheet 11.

Support 12 may have any shape as long as support 12 can cover another surface of thin sheet 11. The shape of support 12 in plan view may be the same as that of thin sheet 11 or may be larger than that of thin sheet 11. For example, support 12 may have a tab or the like for pinching support 12 when separating support 12 from thin sheet 11.

The thickness of support 12 is preferably 50 to 2000 μm, more preferably 100 to 1500 μm. Support 12 having a thickness in this range easily deforms in any direction when being separated from thin sheet 11.

Support 12 is made of a hydrophilic material or a water-absorbent material capable of holding water inside. The term hydrophilic material as used herein refers to a material having a contact angle of 90° or less. The term water-absorbent material as used herein refers to a material having a structure (e.g., pores) capable of holding water inside.

Examples of the material of support 12 include paper (cellulose), rayon, polyester, aramid, glass fiber, nylon, vinylon, polyolefins (e.g., polyethylene, low-density polyethylene, and polypropylene), ethylene vinyl acetate resin, synthetic rubber, copolymer polyamide resin, copolymer polyester resin, porous film, and nanofiber sheet. Of these materials, paper (cellulose), rayon, and polyester are preferred because support 12 is easily separated from thin sheet 11. Support 12 may be optically transmissive or may not be optically transmissive. To distinguish between a surface with thin sheet 11 thereon and a surface without thin sheet 11 thereon, one surface may be colored or may be provided with characters or patterns.

Support 12 preferably has flexibility. Support 12 preferably has an elastic modulus of 100 to 100000 MPa, more preferably has an elastic modulus of 100 to 5000 MPa. The elastic modulus is measured by any one of the static test method, the transverse vibration method, and the ultrasonic method. The JIS standards regarding elastic modulus measurement are JIS Z2280, JIS R1602, and JIS R1605, and the elastic modulus is measured in accordance with any one of these JIS standards. When being separated from thin sheet 11, support 12 having an elastic modulus in this range is unlikely to undergo fracture and the like and can deform to an appropriate degree.

Figure 2A:
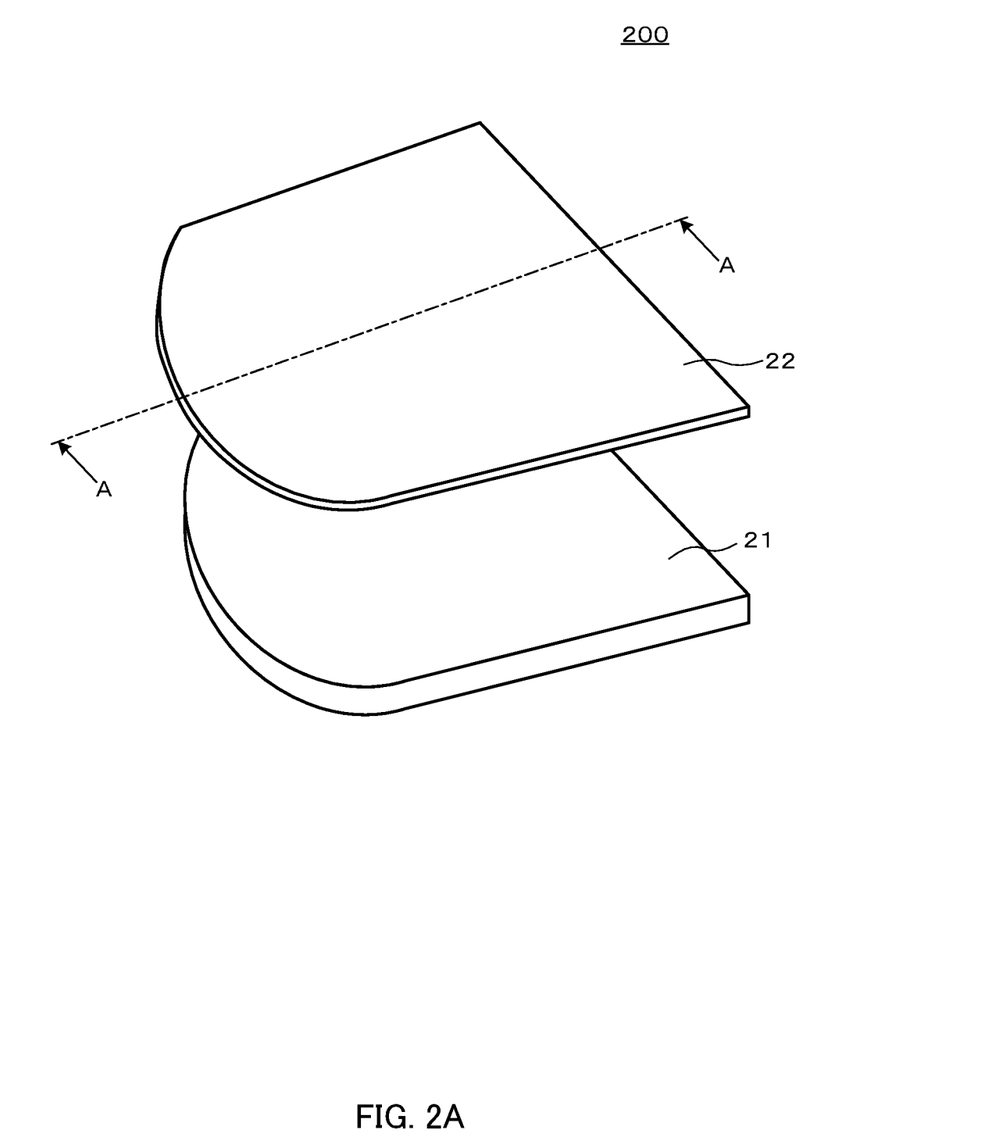
FIG. 2A is an exploded perspective view of a jig according to Embodiment 1 of the present disclosure.

[Jig] Next, the structure of jig 200 according to Embodiment 1 will be described with reference to FIG. 2. Referring to FIG. 2A, jig 200 includes at least substrate 21 and porous hydrophilic film 22 on a first surface of substrate 21.

(Substrate)

Substrate 21 is a member that prevents bending of thin sheet 11 when thin sheet 11 is attached to a target surface. Preferably, substrate 21 has high flexibility and elastically deforms in conformity to the irregularities on the target surface when thin sheet 11 is pressed against the target surface. Substrate 21 thus preferably has an Asker C hardness of 4 degrees or more and 20 degrees or less.

The shape of substrate 21 in plan view is appropriately selected according to, for example, the shape of the target surface and the shape of multilayer sheet 100 (particularly thin sheet 11). Substrate 21 has a larger area than thin sheet 11. Substrate 21 may have a plate shape or may have a curved surface (concave or convex). The details of a preferred shape of the convex R curved surface of the first surface will be described below. Substrate 21 may have any thickness, and preferably has a thickness of about 0.1 to 15 mm, more preferably has a thickness of about 0.1 to 8 mm from the viewpoint of handleability.

Substrate 21 may have transparency or may not have transparency. Substrate 21 preferably has transparency because it is easy to visually recognize the position of thin sheet 11 when attaching thin sheet 11 to the target surface. The term "having transparency" means that, for example, the optical transmittance at a wavelength of 550 mm is 40% or more.

Examples of substrate 21 include a sheet containing, for example, rayon, polyester, aramid, glass fiber, nylon, vinylon, polyolefins (e.g., polyethylene, polypropylene, and low-density polyethylene), ethylene vinyl acetate resin, synthetic rubber, copolymer polyamide resin, or copolymer polyester resin, a silicon (Si)-based sheet containing a hydrophilic agent, an elastomer sheet containing a hydrophilic agent, and a rubber sheet composed of an aqueous gel and the like. These sheets may have been subjected to various hydrophilic treatments.

(Porous Hydrophilic Film)

Porous hydrophilic film 22 is composed of a film-shaped porous hydrophilic member. The contact angle between porous hydrophilic film 22 and water is preferably 90° or less, more preferably 50° or less. In the case where the contact angle between porous hydrophilic film 22 and water is in this range, an aqueous liquid layer is easily uniformly formed on the surface of porous hydrophilic film 22, and the thin sheet is easily brought into close contact with porous hydrophilic film 22.

Porous hydrophilic film 22 has fine pores with a predetermined porosity. The porosity is the proportion of the opening area (fine pores) per unit volume. Example 1 for specifying a preferable porosity range will be described below.

In the case where jig 200 has porous hydrophilic film 22 on the surface, the area of porous hydrophilic film 22 in contact with thin sheet 11 is reduced because of fine pores of porous hydrophilic film 22 to decrease the degree of close contact with thin sheet 11. The aqueous liquid infiltrates into fine pores of porous hydrophilic film 22 to increase the width of the aqueous liquid layer between jig 200 and thin sheet 11. Therefore, thin sheet 11 is easily separated from jig 200, and thin sheet 11 is easily transferred to the target surface.

The shape of porous hydrophilic film 22 in plan view is the same as that of substrate 21 in Embodiment 1. The shape of porous hydrophilic film 22 in plan view is larger than that of thin sheet 11 and may be slightly smaller than that of substrate 21. The thickness of porous hydrophilic film 22 is 500 μm or less, more preferably 100 μm or less.

Porous hydrophilic film 22 may be composed of one layer (monolayer film) or may be composed of two or more layers (multilayer film). For example, porous hydrophilic film 22 may be a multilayer film including a hydrophilic film and a substrate having desired elasticity. The hydrophilic film and the substrate may be bonded to each other with an adhesive or the like. In the case where porous hydrophilic film 22 is a multilayer body having a hydrophilic film and an elastic substrate, porous hydrophilic film 22 conforms to the profile of the thin sheet-attachment surface (target surface) even when the target surface is a curved surface or the like. This configuration enables close contact between the thin sheet and the target surface.

The hydrophilic surface (surface that faces thin sheet 11, surface of jig 200) of porous hydrophilic film 22 may be smooth or uneven.

Porous hydrophilic film 22 may have transparency or may not have transparency. Preferably, porous hydrophilic film 22 and substrate 21 both have transparency because it is easy to visually recognize the position of thin sheet 11 when attaching thin sheet 11 to the target surface.

Examples of porous hydrophilic film 22 include a film containing, for example, rayon, polyester, aramid, glass fiber, nylon, vinylon, polyolefins (e.g., polyethylene, polyethylene terephthalate, polypropylene, and low-density polyethylene), ethylene vinyl acetate resin, synthetic rubber, copolymer polyamide resin, or copolymer polyester resin, a silicon (Si)-based film containing a hydrophilic agent, an elastomer-based film containing a hydrophilic agent, and a rubber-based film composed of an aqueous gel and the like.

Porous hydrophilic film 22 is bonded and fixed to the first surface of substrate 21 with an adhesive (not shown) or the like. The adhesive for bonding substrate 21 and porous hydrophilic film 22 is preferably a hydrophobic adhesive.

Figure 2B:
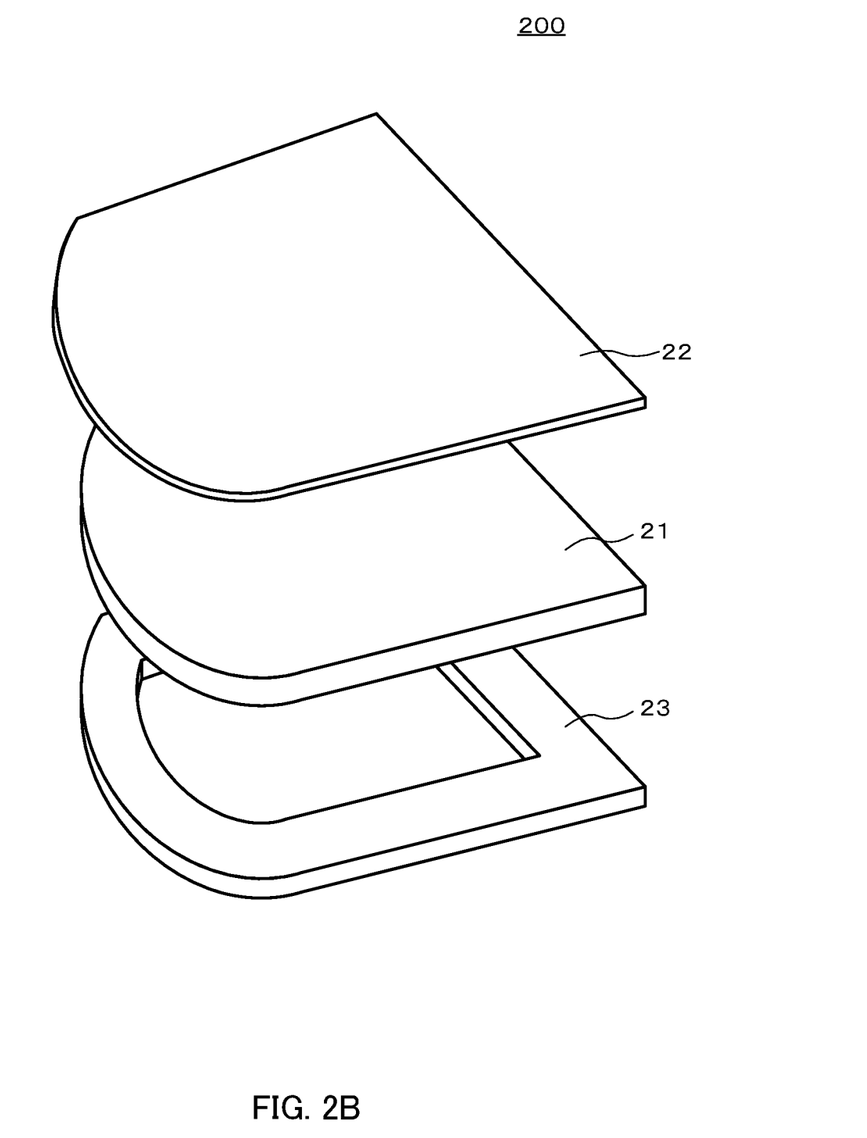
FIG. 2B is an exploded perspective view of a jig according to Embodiment 1 of the present disclosure.

(Base) Referring to FIG. 2B, jig 200 may include a base 23 in addition to substrate 21 and porous hydrophilic film 22.

Base 23 is composed of a soft porous member, such as a sponge structure. Base 23 more preferably has a closed-cell structure (non-water-absorbent structure).

Base 23 has a through-hole in its central portion so as to keep flexibility of substrate 21 in fixing base 23 to substrate 21. In other words, the outer shape of base 23 is a frame shape.

The shape of base 23 in plan view is such that the periphery of base 23 substantially coincides with that of substrate 21 in Embodiment 1. Base 23 may have any thickness, but preferably has a thickness of about 0.1 to 15 mm, more preferably has a thickness of about 0.1 to 8 mm from the viewpoint of handleability. To evenly apply pressure to the target surface, the Asker C hardness of base 23 is preferably 5 degrees or more, more preferably 10 degrees or more.

Examples of the material of base 23 include acrylic resin, PET (polyethylene terephthalate), PC (polycarbonate), and hard vinyl chloride (vinyl chloride).

Base 23 is bonded and fixed to the bottom surface (surface opposite to first surface) of substrate 21 with an adhesive (not shown) or the like. The adhesive for bonding substrate 21 and base 23 is preferably a hydrophobic adhesive.

[Method for Using Multilayer Sheet]

Figure 3A:
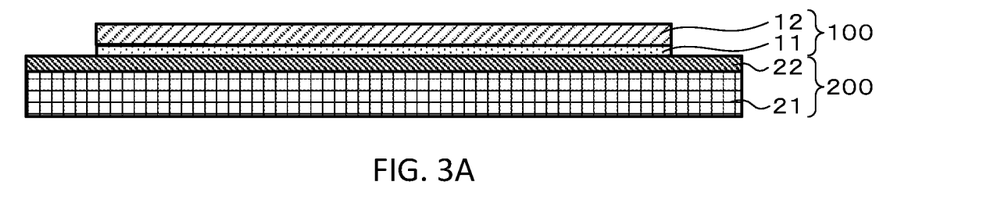
FIGS. 3A to 3C illustrate schematic sectional views of a method for placing a thin sheet of a multilayer sheet on the jig according to Embodiment 1 of the present disclosure.
Figure 3B:
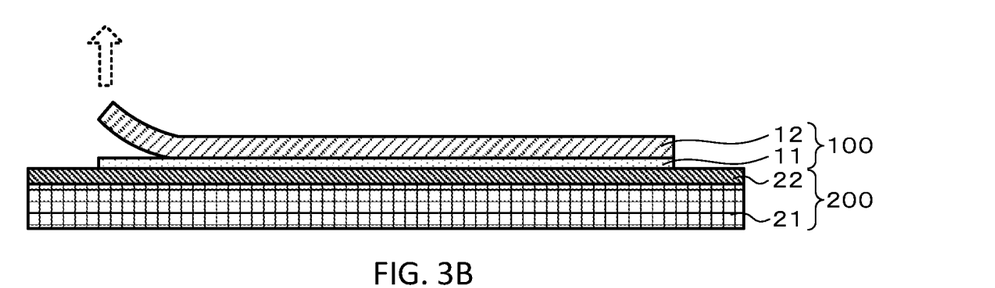
Figure 3C:
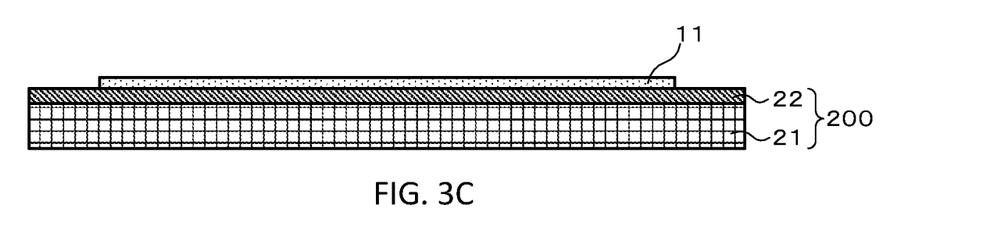

Next, the method for using multilayer sheet 100 according to Embodiment 1 will be described with reference to FIGS. 3A to 3C. FIGS. 3A to 3C are cross-sectional views taken along line A-A in FIGS. 1 and 2A. The method for using multilayer sheet 100 according to Embodiment 1 is not limited to the following method.

Referring to FIG. 3A, a user disposes multilayer sheet 100 on jig 200 such that porous hydrophilic film 22 of jig 200 faces thin sheet 11. In other words, porous hydrophilic film 22 functions as a temporary attachment site for thin sheet 11.

The user then sprays an aqueous liquid with high biosafety, such as water, an emulsion, or a moisturizer, to the entire support 12 of multilayer sheet 100 by using a sprayer or the like. Hydrophilic or water-absorbent support 12 thus absorbs the aqueous liquid to form an aqueous liquid layer (not shown) between support 12 and thin sheet 11 in multilayer sheet 100. At this time, layer-by-layer adsorption between jig 200 and thin sheet 11 impregnated with the aqueous liquid also occurs.

As illustrated in FIG. 3B, the user then lifts support 12 up and separates support 12 from thin sheet 11.

As illustrated in FIG. 3C, the user holds jig 200 and brings thin sheet 11 on jig 200 into close contact with a target surface (not shown). By pressing thin sheet 11 against the target surface using jig 200, the user separates thin sheet 11 from jig 200 and transfers thin sheet 11 to the target surface. At this time, the user elastically deforms substrate 21 in conformity to the irregularities on the target surface to evenly apply pressure to substrate 21 and thus to evenly bring thin sheet 11 into close contact with the target surface.

In the case where thin sheet 11 is transferred to the target surface, the presence of a water layer between thin sheet 11 and porous hydrophilic film 22 of jig 200 facilitates separation of thin sheet 11 from jig 200. As necessary, water may be sprayed to the target surface or thin sheet 11 by using a sprayer or the like to facilitate separation of thin sheet 11 from jig 200.

[Positioning Method]

In the case where substrate 21 and porous hydrophilic film 22 of jig 200 both have transparency, a user can easily recognize the position of thin sheet 11 when attaching thin sheet 11 to a target surface, as described above. Specific examples of the method for positioning thin sheet 11 by using transparent jig 200 will be described below.

First Example

A method in a first example involves positioning thin sheet 11 on a target surface while seeing thin sheet 11 through jig 200. For example, a user positions a concealer-printed area of thin sheet 11 on a dark spot on the skin while seeing thin sheet 11 through jig 200 and presses jig 200 against a central area of the cheekbone.

Second Example

A method in a second example involves making a positioning mark (e.g., dot, line, box) on jig 200 in advance. For example, a mark serving as a guide for indicating a region in which thin sheet 11 is to be disposed is made on substrate 21 or porous hydrophilic film 22 by printing or the like. Alternatively, a mark for indicating a jig 200 section to be pressed against a predetermined area of a target surface (face), such as a central area of the cheekbone or the side of the nose, is made on substrate 21 or porous hydrophilic film 22 by printing or the like.

Third Example

A method in a third example involves using fine pores in porous hydrophilic film 22 of jig 200 as a mark. A jig 200 section to be pressed against a predetermined area of a target surface (face), such as a central area of the cheekbone or the side of the nose, is defined by the location of the fine pores.

Fourth Example

A method in a fourth example involves using the inner periphery of base 23 of jig 200 as a mark. A jig 200 section to be pressed against a predetermined area of a target surface (face), such as a central area of the cheekbone or the side of the nose, is defined by the positional relationship from the inner periphery of base 23.

[Others]

Figure 4:
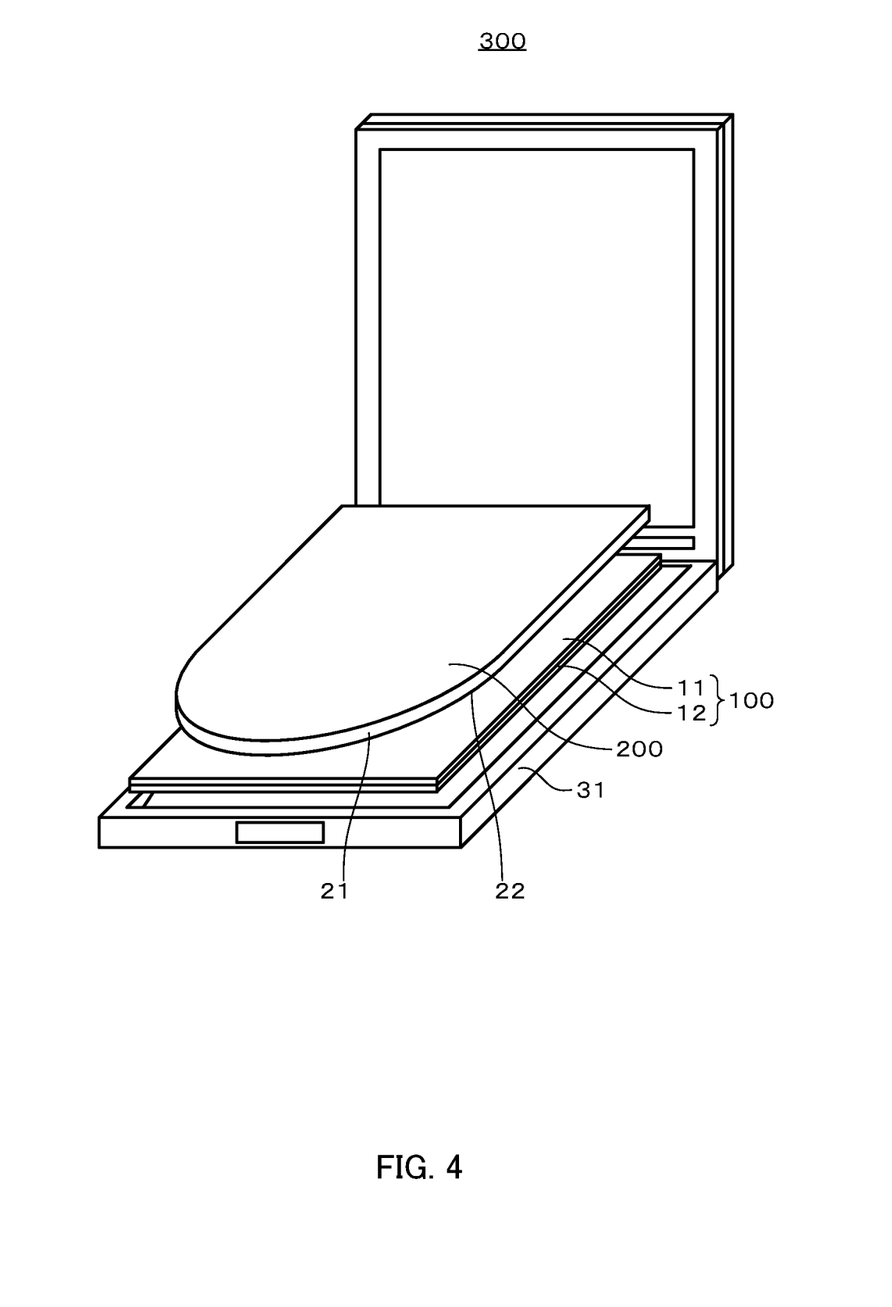
FIG. 4 is a perspective view of a cosmetic set including the jig according to Embodiment 1 of the present disclosure.

Jig 200 according to the present disclosure can also be accommodated in cosmetic set 300. FIG. 4 is a perspective view of cosmetic set 300 including jig 200 according to Embodiment 1.

In cosmetic set 300, multilayer sheet 100 and jig 200 are kept inside housing 31. At this time, multilayer sheet 100 is disposed such that support 12 faces the inner bottom surface of housing 31. Jig 200 is then disposed on thin sheet 11 of multilayer sheet 100 such that porous hydrophilic film 22 faces thin sheet 11.

EXAMPLES

The details of a preferred range of the porosity of fine pores of porous hydrophilic film 22 according to the present disclosure will be described below with reference to Examples. The scope of the present disclosure is not limited by Examples.

Example 1

In Example 1, jig 200 was prepared in which porous hydrophilic film 22 was a monolayer film or a multilayer film, and the porosity A of fine pores of porous hydrophilic film 22 was the value (%) shown in Table 1. The porosity A is calculated from the following expression where D is the diameter of the fine pores and P is the pitch of the fine pores.

$$A = 78.5 \times D^2 / P^2$$

Comparative Example 1

In Comparative Example 1-1, jig 200 was prepared in which a silicone puff (no fine pores) was bonded to substrate 21 instead of porous hydrophilic film 22. In Comparative Example 1-2, jig 200 was prepared in which a hydrophilic film (no fine pores) was bonded to substrate 21 instead of porous hydrophilic film 22.

The following steps were performed over multiple times in Examples and Comparative Examples.

(1) Multilayer sheet 100 is disposed on porous hydrophilic film 22 (silicone puff, hydrophilic film) of jig 200 such that support 12 of multilayer sheet 100 faces upward, and water is sprayed to support 12.

(2) Support 12 is then separated from thin sheet 11, and thin sheet 11 is attached to a target surface by using jig 200.

[Evaluation]

The following items were evaluated for Examples and Comparative Examples described above. The results are shown in Table 1. In each item, the evaluation value "A" indicates a level without any problem. The evaluation value "B" indicates a practically acceptable level lower than "A". The evaluation value "C" indicates a practically problematic level.

<Item 1: Transfer to Skin>

Whether thin sheet 11 is easily transferred to the skin (target surface).
  A: Thin sheet 11 is easily transferred to the skin from jig 200.
  B: Thin sheet 11 adheres to part of jig 200 and may be difficult to separate from jig 200.
  C: Thin sheet 11 is not separated from jig 200 and cannot be transferred to the skin.

<Item 2: Evenness of Pressure>

Whether pressure is evenly applied to thin sheet 11 from one end to the other end of jig 200 when thin sheet 11 is pressed against the skin by using jig 200.
  A: Pressure is evenly applied to thin sheet 11.
  B: Some area is not subjected to sufficient pressure because of irregularities on the face. Thin sheet 11 thus needs to be attached to the skin with the lifting area pressed by hand.
  C: Many areas lift without pressure, and it is difficult to attach thin sheet 11 to the skin even by pressing thin sheet 11 by hand.

<Item 3: Wrinkling>

Whether thin sheet 11 wrinkles when being transferred to the skin.
  A: Thin sheet 11 does not wrinkle at all.
  B: Thin sheet 11 may wrinkle.
  C: Thin sheet 11 inevitably wrinkles.

<Item 4: Disposition on Jig>

Whether thin sheet 11 is easily disposed on jig 200.
  A: Thin sheet 11 can be disposed on jig 200 so as to be in close contact with jig 200.
  B: Thin sheet 11 may partially lift from jig 200 when being disposed on jig 200.
  C: Thin sheet 11 entirely lifts from jig 200 and cannot be disposed on jig 200.

<Item 5: Spread of Water>

Whether sprayed water is easily spread from a central portion to a peripheral portion of multilayer sheet 100.
  A: Water is evenly spread over the entire multilayer sheet 100.
  B: Water is difficult to spread and may need to be additionally sprayed.
  C: Water is not spread on multilayer sheet 100.

<Item 6: Separation of Support>

Whether support 12 is easily separated from thin sheet 11.
  A: Support 12 can be easily separated from thin sheet 11.
  B: Support 12 may partially adhere to thin sheet 11 and may be difficult to separate from thin sheet 11.
  C: Support 12 entirely adheres to thin sheet 11, and it is difficult to separate support 12 from thin sheet 11.

<Item 7: Impregnation of Porous Hydrophilic Film with Water>

Whether a water layer is sufficiently spread between thin sheet 11 and porous hydrophilic film 22 when water is sprayed.

A: A water layer is spread evenly and entirely between thin sheet 11 and porous hydrophilic film 22.

B: A water layer is insufficient between thin sheet 11 and porous hydrophilic film 22, and water may need to be additionally sprayed.

C: A water layer is not spread between thin sheet 11 and porous hydrophilic film 22.

TABLE 1

|  | Comparative Example 1-1 | Comparative Example 1-2 | Example 1 Monolayer Film | | | | Example 1 Multilayer Film | | | | | |
|---|---|---|---|---|---|---|---|---|---|---|---|---|
| A | — | — | 35 | 40 | 50 | 5 | 35 | 41 | 46 | 50 | 55 | 95 |
| 1. Transfer to skin | C | B | A | A | A | B | A | A | A | A | A | C |
| 2. Evenness of pressure | B | B | A | A | A | B | A | A | A | A | A | B |
| 3. Wrinkling | C | C | A | A | A | C | A | A | A | A | A | C |
| 4. Disposition on jig | A | A | A | A | A | A | A | A | A | A | A | A |
| 5. Spread of water | C | B | A | A | A | B | A | A | A | A | A | C |
| 6. Separation of support | C | A | A | A | A | A | A | A | A | A | A | C |
| 7. Impregnation of porous hydrophilic film with water | C | B | A | A | A | B | A | A | A | A | A | C |

[Results]

As shown in Table 1, Example 1 having fine pores with a predetermined porosity showed better evaluation values than Comparative Examples without fine pores, regardless of monolayer film or multilayer film. In the case where the porosity A was in the range of 35% A 55%, the evaluation value was "A" for all items.

Advantageous Effects

As described above, porous hydrophilic film 22 of jig 200 has fine pores with a predetermined porosity according to Example 1 of Embodiment 1. When water is sprayed to multilayer sheet 100, water is easily spread from a central portion to a peripheral portion of multilayer sheet 100, and a water layer is easily spread between thin sheet 11 and porous hydrophilic film 22. Water is thus evenly spread over the entire multilayer sheet 100. Therefore, thin sheet 11 can be easily transferred to a target surface from jig 200.

In the case where substrate 21 of jig 200 has flexibility, pressure can be evenly applied to a target surface, and thin sheet 11 can be evenly brought into close contact with the target surface. Therefore, thin sheet 11 can be easily attached to the target surface.

Example 2

In Example 2, jig 200 was prepared in which a first surface of substrate 21 was a convex R curved surface, and the radius of curvature R was a value (R=10, 30, 40, 50, 70, 90, 150, 160 (unit: mm)) shown in Table 2. Substrate 21 preferably has stiffness sufficient to prevent significant distortion caused by the reaction force from the target surface when thin sheet 11 is pressed against the target surface. For this, substrate 21 preferably has a thickness in the range of 6 mm or more and 50 mm or less.

Comparative Example 2-1

In Comparative Example 2-1, jig 200 was prepared in which a first surface of substrate 21 was a flat surface, and a silicone puff was bonded to substrate 21 instead of hydrophilic film 22. In Comparative Example 2-2, jig 200 was prepared in which a first surface of substrate 21 was a flat surface, and hydrophilic film 22 was bonded to substrate 21.

The following steps were performed over multiple times in Examples and Comparative Examples.

(1) Multilayer sheet 100 is disposed on hydrophilic film 22 (silicone puff) of jig 200 such that support 12 of multilayer sheet 100 faces upward, and water is sprayed to support 12.

(2) Support 12 is then separated from thin sheet 11, and thin sheet 11 is attached to a target surface by using jig 200.

[Evaluation]

The following items were evaluated for Example 2 and Comparative Example 2 described above. The results are shown in Table 2. In each item, the evaluation value "A" indicates a level without any problem. The evaluation value "B" indicates a practically acceptable level lower than "A". The evaluation value "C" indicates a practically problematic level.

<Item 1: Transfer to Skin>

Whether thin sheet 11 is easily transferred to the skin (target surface).

A: Thin sheet 11 is easily transferred to the skin from jig 200.

B: Thin sheet 11 adheres to part of jig 200 and may be difficult to separate from jig 200.

C: Thin sheet 11 is not separated from jig 200 and cannot be transferred to the skin.

<Item 2: Evenness of Pressure>

Whether pressure is evenly applied to thin sheet 11 from one end to the other end of jig 200 when thin sheet 11 is pressed against the skin by using jig 200.

A: Pressure is evenly applied to thin sheet 11.

B: Some area is not subjected to sufficient pressure because of irregularities on the face. Thin sheet 11 thus needs to be attached to the skin with the lifting area pressed by hand.

C: Many areas lift without pressure, and it is difficult to attach thin sheet 11 to the skin even by pressing thin sheet 11 by hand.

<Item 3: Wrinkling>

Whether thin sheet 11 wrinkles when being transferred to the skin.

A: Thin sheet 11 does not wrinkle at all.

B: Thin sheet 11 may wrinkle.

C: Thin sheet 11 inevitably wrinkles.

<Item 4: Disposition on Jig>
  Whether thin sheet 11 is easily disposed on jig 200.
  A: Thin sheet 11 can be disposed on jig 200 so as to be in close contact with jig 200.
  B: Thin sheet 11 may partially lift from jig 200 when being disposed on jig 200.
  C: Thin sheet 11 entirely lifts from jig 200 and cannot be disposed on jig 200.
<Item 5: Spread of Water>
  Whether sprayed water is easily spread from a central portion to a peripheral portion of multilayer sheet 100.
  A: Water is evenly spread over the entire multilayer sheet 100.
  B: Water is difficult to spread and may need to be additionally sprayed.
  C: Water is not spread on multilayer sheet 100.
<Item 6: Separation of Support>
  Whether support 12 is easily separated from thin sheet 11.
  A: Support 12 can be easily separated from thin sheet 11.
  B: Support 12 may partially adhere to thin sheet 11 and may be difficult to separate from thin sheet 11.
  C: Support 12 entirely adheres to thin sheet 11, and it is difficult to separate support 12 from thin sheet 11.
<Item 7: Impregnation of Hydrophilic Film with Water>
  Whether a water layer is sufficiently spread between thin sheet 11 and hydrophilic film 22 when water is sprayed.
  A: A water layer is spread evenly and entirely between thin sheet 11 and hydrophilic film 22.
  B: A water layer is insufficient between thin sheet 11 and hydrophilic film 22, and water may need to be additionally sprayed.
  C: A water layer is not spread between thin sheet 11 and hydrophilic film 22.

contact with the target surface. Therefore, thin sheet 11 can be easily attached to the target surface.

When water is sprayed to multilayer sheet 100 in the case where the first surface of jig 200 has a convex R curved surface, water is easily spread from a central portion to a peripheral portion of multilayer sheet 100, and a water layer is easily spread between thin sheet 11 and hydrophilic film 22. Water is thus evenly spread over the entire multilayer sheet 100. Therefore, thin sheet 11 can be easily transferred to a target surface from jig 200.

Embodiment 2

In Embodiment 2, the structure without substrate 21 in jig 200 according to Embodiment 1 will be described below.
[Multilayer Sheet]
The structure of a multilayer sheet according to Embodiment 2 is the same as multilayer sheet 100 described in Embodiment 1 (FIG. 1), and description of the structure is omitted.

Next, the structure of film jig 400 (see FIG. 5) according to Embodiment 2 will be described. Film jig 400 has no substrate 21 and includes only porous hydrophilic film 22 compared with jig 200 described in Embodiment 1 (FIG. 2A).
(Porous Hydrophilic Film)
Preferably, porous hydrophilic film 22 according to Embodiment 2 has high flexibility and elastically deforms in conformity to the irregularities on the target surface when thin sheet 11 is pressed against the target surface. Porous hydrophilic film 22 thus preferably has an Asker C hardness of 4 degrees or more and 20 degrees or less.

TABLE 2

|  | Comparative Example 2-1 | Comparative Example 2-2 | Example 2 | | | | | | | |
|---|---|---|---|---|---|---|---|---|---|---|
| R | — | — | 10 | 30 | 40 | 50 | 70 | 90 | 150 | 160 |
| 1. Transfer to skin | C | B | B | A | A | A | A | A | A | B |
| 2. Evenness of pressure | B | B | B | A | A | A | A | A | A | B |
| 3. Wrinkling | C | C | B | A | A | A | A | A | A | B |
| 4. Disposition on jig | A | A | C | B | A | A | A | A | A | A |
| 5. Spread of water | C | B | B | B | A | A | A | A | B | B |
| 6. Separation of support | C | A | A | A | A | A | A | A | A | A |
| 7. Impregnation of porous hydrophilic film with water | C | B | B | B | A | A | A | A | B | B |

[Results]

As shown in Table 2, Example 2 in which the first surface was a convex R curved surface showed better evaluation values than Comparative Examples in which the first surface was a flat surface. In the case where the radius of curvature R was in the range of 30≤R≤150, the evaluation value was "A" for items 1 to 3 regarding attachment to the skin. In the case where the radius of curvature R was in the range of 40≤R≤90, the evaluation value was "A" for all items.

Advantageous Effects

As described above, the first surface of jig 200 may have a convex R curved surface according to Example 2 of Embodiment 1. With this configuration, a user can roll jig 200 parallel to a target surface by using the convex R curved surface on the surface of jig 200 to evenly apply pressure to the target surface and to evenly bring thin sheet 11 into close Porous hydrophilic film 22 has transparency because it is easy to visually recognize the position of thin sheet 11 when attaching thin sheet 11 to the target surface. The term "having transparency" means that, for example, the optical transmittance at a wavelength of 550 mm is 40% or more.

Other features of porous hydrophilic film 22 according to Embodiment 2 are the same as in Embodiment 1, and detailed description thereof is omitted.
[Method for Using Multilayer Sheet]

Next, the method for using multilayer sheet 100 according to Embodiment 2 will be described with reference to FIGS. 5A to 5C. The method for using multilayer sheet 100 according to Embodiment 2 is not limited to the following method.

Figure 5A:
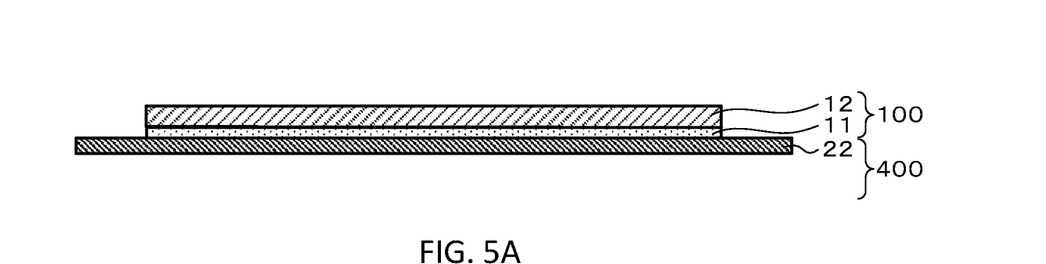
FIGS. 5A to 5C illustrate schematic sectional views of a method for placing a thin sheet of a multilayer sheet on a film jig according to Embodiment 2 of the present disclosure.

Referring to FIG. 5A, a user disposes multilayer sheet 100 on film jig 400 such that porous hydrophilic film 22 of film jig 400 faces thin sheet 11. In other words, porous hydrophilic film 22 functions as a temporary attachment site for thin sheet 11.

The user then sprays an aqueous liquid with high biosafety, such as water, an emulsion, or a moisturizer, to the entire support 12 of multilayer sheet 100 by using a sprayer or the like. Hydrophilic or water-absorbent support 12 thus absorbs an aqueous liquid to form an aqueous liquid layer (not shown) between support 12 and thin sheet 11 in multilayer sheet 100. At this time, layer-by-layer adsorption between film jig 400 and thin sheet 11 impregnated with the aqueous liquid also occurs.

Figure 5B:
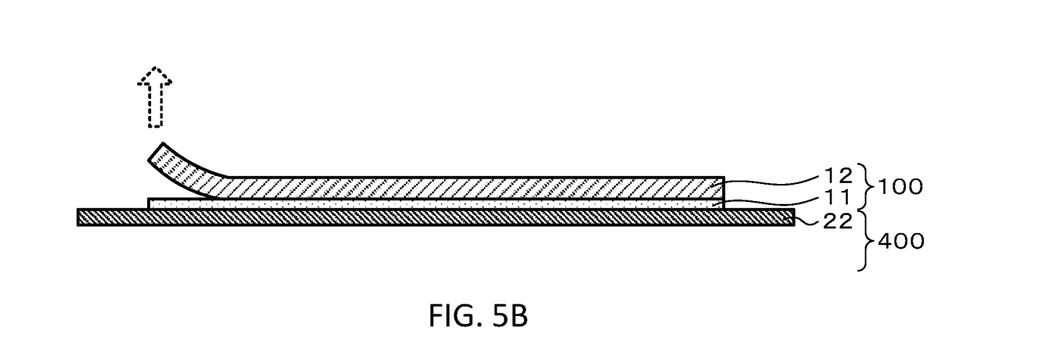

As illustrated in FIG. 5B, the user then lifts support 12 up and separates support 12 from thin sheet 11.

Figure 5C:
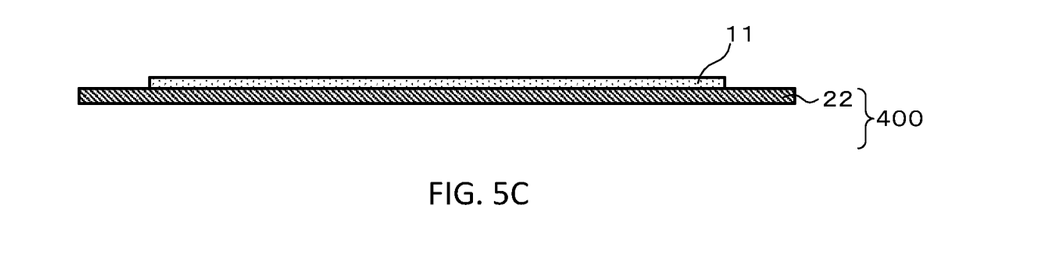

As illustrated in FIG. 5C, the user holds film jig 400 and brings thin sheet 11 on film jig 400 into close contact with a target surface (not shown). By pressing thin sheet 11 against the target surface using film jig 400, the user separates thin sheet 11 from film jig 400 and transfers thin sheet 11 to the target surface. At this time, the user elastically deforms substrate 21 in conformity to the irregularities on the target surface to evenly apply pressure to substrate 21 and thus to evenly bring thin sheet 11 into close contact with the target surface.

In the case where thin sheet 11 is transferred to the target surface, the presence of a water layer between thin sheet 11 and porous hydrophilic film 22 of film jig 400 facilitates separation of thin sheet 11 from film jig 400. As necessary, water may be sprayed to the target surface or thin sheet 11 by using a sprayer or the like to facilitate separation of thin sheet 11 from film jig 400.

[Positioning Method]

In the case where porous hydrophilic film 22 has transparency, the user can easily recognize the position of thin sheet 11 when attaching thin sheet 11 to a target surface, as described above. In Embodiment 2, thin sheet 11 can be positioned by using transparent film jig 400 in accordance with the positioning methods in the first example to the third example illustrated in Embodiment 1.

[Others]

Like jig 200 described in Embodiment 1 (FIG. 4), film jig 400 according to the present disclosure can also be accommodated in cosmetic set 300.

EXAMPLES

The details of a preferred range of the porosity of fine pores of porous hydrophilic film 22 according to the present disclosure will be described below with reference to Examples. The scope of the present disclosure is not limited by Examples.

Example 3

In Example 3, film jig 400 was prepared in which porous hydrophilic film 22 was a monolayer film or a multilayer film, and the porosity A of fine pores of porous hydrophilic film 22 was the value (%) shown in Table 1. The porosity A is calculated from the following expression where D is the diameter of the fine pores and P is the pitch of the fine pores.

$$A = 78.5 \times D^2/P^2$$

Comparative Example 3

In Comparative Example 3, film jig 400 including a hydrophilic film (no fine pores) instead of porous hydrophilic film 22 was prepared.

The following steps were performed over multiple times in Examples and Comparative Examples.

(1) Multilayer sheet 100 is disposed on porous hydrophilic film 22 (silicone puff, hydrophilic film) of film jig 400 such that support 12 of multilayer sheet 100 faces upward, and water is sprayed to support 12.

(2) Support 12 is then separated from thin sheet 11, and thin sheet 11 is attached to a target surface by using film jig 400.

[Evaluation]

The following items were evaluated for Examples and Comparative Examples described above. The results are shown in Table 3. In each item, the evaluation value "A" indicates a level without any problem. The evaluation value "B" indicates a practically acceptable level lower than "A". The evaluation value "C" indicates a practically problematic level.

<Item 1: Transfer to Skin>

Whether thin sheet 11 is easily transferred to the skin (target surface).
  A: Thin sheet 11 is easily transferred to the skin from film jig 400.
  B: Thin sheet 11 adheres to part of film jig 400 and may be difficult to separate from film jig 400.
  C: Thin sheet 11 is not separated from film jig 400 and cannot be transferred to the skin.

<Item 2: Evenness of Pressure>

Whether pressure is evenly applied to thin sheet 11 from one end to the other end of film jig 400 when thin sheet 11 is pressed against the skin by using film jig 400.
  A: Pressure is evenly applied to thin sheet 11.
  B: Some area is not subjected to sufficient pressure because of irregularities on the face. Thin sheet 11 thus needs to be attached to the skin with the lifting area pressed by hand.
  C: Many areas lift without pressure, and it is difficult to attach thin sheet 11 to the skin even by pressing thin sheet 11 by hand.

<Item 3: Wrinkling>

Whether thin sheet 11 wrinkles when being transferred to the skin.
  A: Thin sheet 11 does not wrinkle at all.
  B: Thin sheet 11 may wrinkle.
  C: Thin sheet 11 inevitably wrinkles.

<Item 4: Disposition on Jig>

Whether thin sheet 11 is easily disposed on film jig 400.
  A: Thin sheet 11 can be disposed on film jig 400 so as to be in close contact with film jig 400.
  B: Thin sheet 11 may partially lift from film jig 400 when being disposed on film jig 400.
  C: Thin sheet 11 entirely lifts from film jig 400 and cannot be disposed on film jig 400.

<Item 5: Spread of Water>

Whether sprayed water is easily spread from a central portion to a peripheral portion of multilayer sheet 100.
  A: Water is evenly spread over the entire multilayer sheet 100.
  B: Water is difficult to spread and may need to be additionally sprayed.
  C: Water is not spread on multilayer sheet 100.

<Item 6: Separation of Support>

Whether support 12 is easily separated from thin sheet 11.
  A: Support 12 can be easily separated from thin sheet 11.
  B: Support 12 may partially adhere to thin sheet 11 and may be difficult to separate from thin sheet 11.
  C: Support 12 entirely adheres to thin sheet 11, and it is difficult to separate support 12 from thin sheet 11.

<Item 7: Impregnation of Porous Hydrophilic Film with Water>

Whether a water layer is sufficiently spread between thin sheet 11 and porous hydrophilic film 22 when water is sprayed.

A: A water layer is spread evenly and entirely between thin sheet 11 and porous hydrophilic film 22.

B: A water layer is insufficient between thin sheet 11 and porous hydrophilic film 22, and water may need to be additionally sprayed.

C: A water layer is not spread between thin sheet 11 and porous hydrophilic film 22.

TABLE 3

| | Comparative Example 3 | Example 3 | | | | | | | | | |
|---|---|---|---|---|---|---|---|---|---|---|---|
| | | Monolayer Film | | | Multilayer Film | | | | | | |
| A | — | 35 | 40 | 50 | 5 | 35 | 41 | 46 | 50 | 55 | 95 |
| 1. Transfer to skin | B | A | A | A | B | A | A | A | A | A | C |
| 2. Evenness of pressure | B | A | A | A | B | A | A | A | A | A | B |
| 3. Wrinkling | C | A | A | A | C | A | A | A | A | A | C |
| 4. Disposition on jig | A | A | A | A | A | A | A | A | A | A | A |
| 5. Spread of water | B | A | A | A | B | A | A | A | A | A | C |
| 6. Separation of support | A | A | A | A | A | A | A | A | A | A | C |
| 7. Impregnation of porous hydrophilic film with water | B | A | A | A | B | A | A | A | A | A | C |

[Results]

As shown in Table 3, Example 3 having fine pores with a predetermined porosity showed better evaluation values than Comparative Example 3 without fine pores, regardless of monolayer film or multilayer film. In the case where the porosity A was in the range of 35% A 55%, the evaluation value was "A" for all items.

Advantageous Effects

As described above, porous hydrophilic film 22 of film jig 400 has fine pores with a predetermined porosity according to Embodiment 2. When water is sprayed to multilayer sheet 100, water is easily spread from a central portion to a peripheral portion of multilayer sheet 100, and a water layer is easily spread between thin sheet 11 and porous hydrophilic film 22. Water is thus evenly spread over the entire multilayer sheet 100. Therefore, thin sheet 11 can be easily transferred to a target surface from film jig 400.

Since porous hydrophilic film 22 of film jig 400 is porous, porous hydrophilic film 22 has more flexibility than a hydrophilic film without fine pores, and simple porous hydrophilic film 22 without substrate 21 allows even application of pressure to a target surface, so that thin sheet 11 can be evenly brought into close contact with the target surface. Therefore, thin sheet 11 can be easily attached to the target surface.

The material of film jig 400 is not limited to a film as long as it is a flexible member, and film jig 400 may be a plate-shaped member processed so as to have a porous hydrophilic surface.

The disclosure of Japanese Patent Application No. 2020-055790, filed on Mar. 26, 2020 and Japanese Patent Application No. 2020-058596, filed on Mar. 27, 2020, including the specification, drawings and abstract, are incorporated herein by reference in its entirety.

INDUSTRIAL APPLICABILITY

A jig according to the present disclosure facilitates attachment of a thin sheet to a target surface. The jig according to the present disclosure is very useful for attachment of various beauty sheets and medical sheets.

REFERENCE SIGNS LIST

100 Multilayer sheet
11 Thin sheet
12 Support
200 Jig
21 Substrate
22 Porous hydrophilic film
23 Base
400 Film jig

The invention claimed is:

1. A jig that assists in attaching a thin sheet to a target surface, the jig comprising:
    a substrate having a first surface;
    a porous hydrophilic film which is attached to the first surface of the substrate,
    wherein the porous hydrophilic film has an Asker C hardness of 4 degrees or more and 20 degrees or less; and
    a base that is attached to a surface of the substrate opposite to the first surface, wherein the base has a frame-shaped outer shape.

2. A jig that assists in attaching a thin sheet to a target surface, the jig comprising:
    a substrate having a first surface;
    a porous hydrophilic film which is attached to the first surface of the substrate, wherein the porous hydrophilic film has pores with a porosity of 35% or more and 55% or less; and
    a base that is attached to a surface of the substrate opposite to the first surface, wherein the base has a frame-shaped outer shape.

3. A jig that assists in attaching a thin sheet to a target surface, the jig comprising:
    a substrate having a first surface, wherein the substrate has an Asker C hardness of 4 degrees or more and 20 degrees or less;
    a porous hydrophilic film which is attached to the first surface of the substrate; and
    a base that is attached to a surface of the substrate opposite to the first surface, wherein the base has a frame-shaped outer shape.

4. The jig according to claim 1, wherein the porous hydrophilic film has transparency.

5. A jig that assists in attaching a thin sheet to a target surface, the jig comprising:
- a substrate having a first surface;
- a porous hydrophilic film which is attached to the first surface of the substrate; and
- a base that is attached to a surface of the substrate opposite to the first surface,
- wherein the base has a frame-shaped outer shape,
- and wherein the base has an Asker C hardness of 5 degrees or more.

6. The jig according to claim 1, wherein the substrate has transparency.

7. The jig according to claim 1, wherein the substrate includes a convex R curved surface.

8. The jig according to claim 1, wherein the substrate entirely has a convex R curved surface.

9. The jig according to claim 7, wherein the convex R curved surface has a radius of curvature R of 30 mm or more and 150 mm or less.

10. The jig according to claim 7, wherein the convex R curved surface has a radius of curvature R of 40 mm or more and 90 mm or less.

11. The jig according to claim 1, wherein the base has a through-hole in a central portion.

* * * * *